United States Patent
Boulais

(10) Patent No.: US 7,192,396 B2
(45) Date of Patent: Mar. 20, 2007

(54) SYSTEM AND METHOD FOR ORIENTING ENDOSCOPE AND OPERATOR CONTROL

(75) Inventor: Dennis R. Boulais, Danielson, CT (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/820,623

(22) Filed: Apr. 8, 2004

(65) Prior Publication Data
US 2005/0228228 A1 Oct. 13, 2005

(51) Int. Cl.
*A61B 1/00* (2006.01)
(52) U.S. Cl. .............. 600/118; 600/102; 600/125; 600/131
(58) Field of Classification Search ........... 600/102, 600/118, 125, 131
See application file for complete search history.

(56) References Cited

U.S. PATENT DOCUMENTS

| | | | |
|---|---|---|---|
| 5,395,381 A | | 3/1995 | Green et al. |
| 5,441,042 A | * | 8/1995 | Putman ............... 600/102 |
| 5,876,332 A | * | 3/1999 | Looney ............... 600/227 |
| 6,805,664 B2 | * | 10/2004 | Doyle et al. ......... 600/102 |
| 6,830,545 B2 | * | 12/2004 | Bendall ............... 600/114 |
| 2002/0133077 A1 | | 9/2002 | Edwardsen et al. |
| 2003/0212308 A1 | | 11/2003 | Bendall |
| 2004/0220449 A1 | * | 11/2004 | Zirps et al. .......... 600/104 |

FOREIGN PATENT DOCUMENTS

WO WO 2004/021868 A2 3/2004

* cited by examiner

*Primary Examiner*—Linda C. M. Dvorak
*Assistant Examiner*—Matthew J. Kasztejna
(74) *Attorney, Agent, or Firm*—Christensen O'Connor Johnson Kindness PLLC

(57) ABSTRACT

A system and method for orienting an endoscope shaft and operator control module. The operator control module includes an engaging mechanism that allows the operator control module to be disengaged from the endoscope shaft. This allows the operator control module to remain in the operator's preferred orientation and then be re-engaged to the endoscope shaft. Remotely powered tip articulation cables are also provided, thus allowing the operator control module the freedom of not having to remain mechanically attached to the endoscope shaft in a fixed position. When the operator wants to rotate the endoscope shaft axially and does not want the position of the operator control module to be changed, the operator control module engaging mechanism is disengaged, after which the endoscope shaft is rotated to the desired position, and the engaging mechanism is then re-engaged to the endoscope shaft or to a fixed feature on the shaft.

3 Claims, 2 Drawing Sheets

SYSTEM AND METHOD FOR ORIENTING ENDOSCOPE AND OPERATOR CONTROL

FIELD OF THE INVENTION

The present invention relates to medical devices, and in particular to endoscopes.

BACKGROUND OF THE INVENTION

Endoscopic procedures for treating abnormal pathologies within the alimentary canal system and biliary (including the biliary, hepatic, and pancreatic ducts) are increasing in number. The endoscope provides access to the general area of a desired duct using direct visualization. In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate to the area to receive treatment. At this point, the endoscope allows other components, such as a catheter, to access the targeted area.

In conjunction with the endoscope, an operator control module is provided that allows a user to control and steer the operation of the endoscope. In certain known endoscopes, the operator control module is permanently fixed to the shaft of the endoscope. In other words, the endoscope shaft is allowed to rotate with respect to the operator control module. This presents awkward ergonomic problems for the operator in that the endoscope shaft must be rotated during the course of endoscopic procedures in order to align the working portions of the endoscope tip to perform functions (e.g., polyp removal, drainage, etc.). In other words, if the operator control module is in a fixed position with respect to the shaft at the endoscope, then the operator sometimes has to try to operate the controls when they are facing away from the operator or are under the shaft and cannot be seen. Because the controls generally have a manually operated tip positioning method, the endoscope shaft cannot be rotated independently from the operator control module, in that the cables that manipulate the endoscope tip are terminated inside the operator control module.

The present invention is directed to an apparatus that overcomes the foregoing and other disadvantages. More specifically, the present invention is directed to a system and method that allows the endoscope shaft to be rotated and the operator control module to be disengaged from the endoscope shaft so that it can remain in the operator's preferred orientation and then re-engaged to the shaft.

SUMMARY OF THE INVENTION

The present invention is directed to a system and method for orienting an endoscope and operator control. In accordance with one aspect of the invention, the endoscope shaft can be rotated and the operator control module can be disengaged from the endoscope shaft, so that the operator control module can remain in the operator's preferred orientation, and then re-engaged to the shaft. It will be appreciated that the disengaging and re-engaging ability is an improvement over known endoscope systems in which the operator is required to twist the fixed operator control module as a way to apply torque to the shaft and rotate axially to achieve the desired tip orientation in the patient, which can thus cause the controls to be facing away from the operator or under the shaft where they cannot be seen.

In accordance with another aspect of the invention, remotely powered tip articulation cables are provided. The remotely powered tip articulation cables provide the operator control module with the freedom to not have to remain mechanically attached to the endoscope shaft in a fixed position.

In accordance with another aspect of the invention, the operator control module may be attached to a rotary union on a fixed feature on the endoscope shaft (e.g., a break-out box). In another embodiment, the operator control module may be directly clamped to the endoscope shaft. As noted above, the ability of the operator control module to be disengaged and re-engaged from the endoscope shaft allows the operator control module to have a selectable orientation with regard to the endoscope shaft.

In accordance with another aspect of the invention, the means for disengaging the operator control module from the endoscope shaft may comprise manually or remotely opening a caliper style set of pads in the operator control module from contact with the endoscope shaft. In another embodiment the means of disengaging may include manually or remotely moving a "C" style clamping device built into the operator control module away from contact with the endoscope shaft. In another embodiment, the means of disengaging may include manually or remotely moving a disengaging one-half of a clutch built into the operator control module with the other half of the clutch built into the a break-out box or other fixed feature on the shaft. In another embodiment, the means of disengaging may include manually or remotely moving a disengaging pressure pad that is mounted to a break-out box or other fixed feature on the shaft.

In accordance with another aspect of the invention, the operator control module may either be wired back to the control box or may have a wireless method to communicate the commands of the operator back to the hardware in the control box. The control box generally includes pumps, a motor, valves, and other devices necessary to provide the standard operation and features in the endoscope.

In accordance with another aspect of the invention, the operator control module is able to be completely detached from the break-out box or endoscope shaft such that it can be cleaned and reused.

In accordance with another aspect of the invention, a method for operating the operator control module with respect to the endoscope shaft is provided. When the operator wants to rotate the endoscope axially and does not want to change the position of the operator control module, the operator first disengages the operator control module clamping means. The shaft is then rotated to the desired orientation. The operator then re-engages the operator control module clamping means to the endoscope shaft or fixed feature on the shaft.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
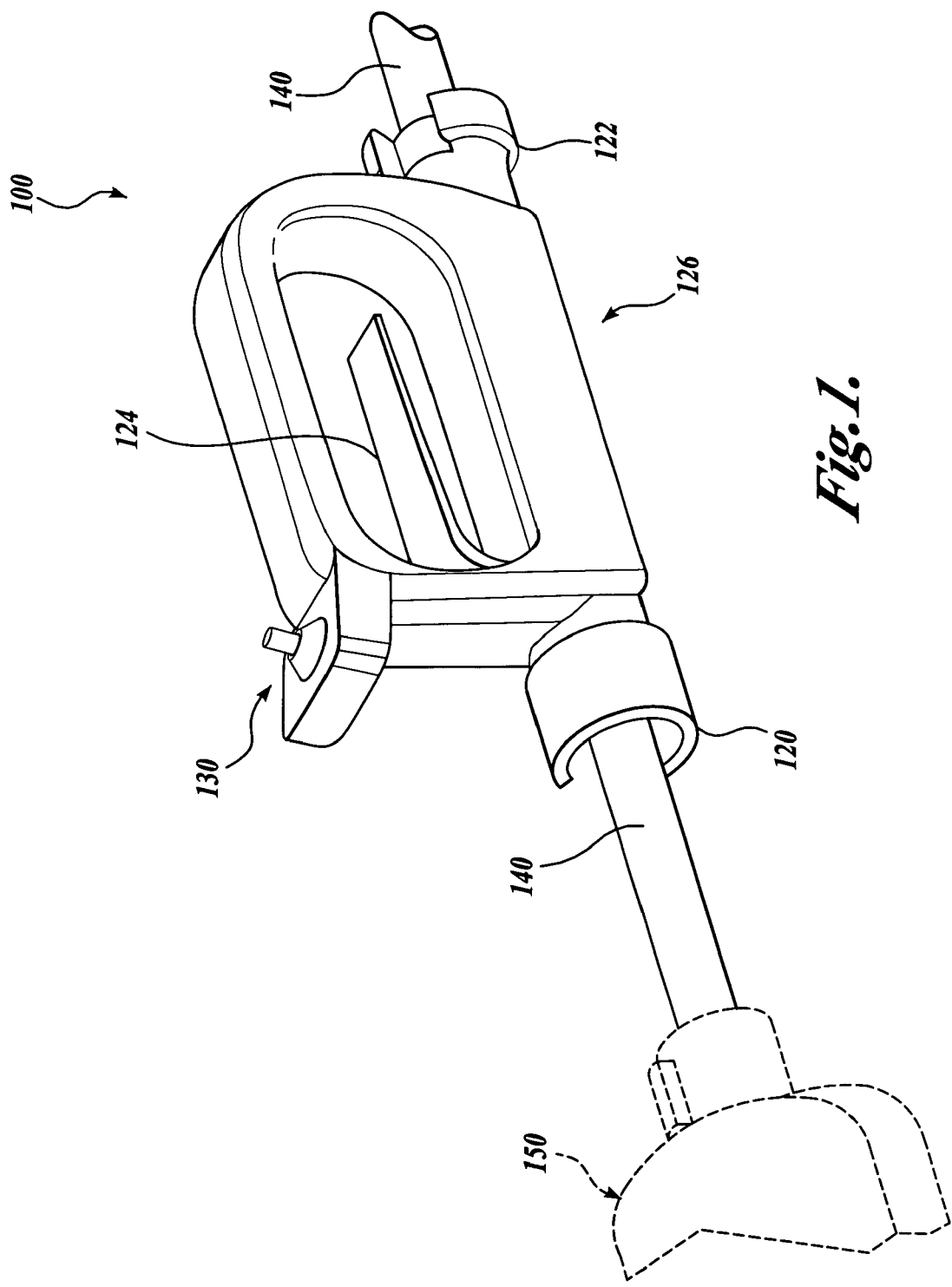
FIG. 1 shows an operator control module including a rotating locking collar to attach to the proximal end of a break-out box for attachment to an endoscope.

FIG. 1 is a diagram of an operator control module 100 that is formed in accordance with the present invention. The operator control module 100 includes an engaging mechanism 120 for fixedly engaging the operator control module 100 to an endoscope shaft 140. In the embodiment shown in FIG. 1, the engaging mechanism 120 is a rotating locking collar which is designed to be attached to the proximal end of a break-out box 150 of the endoscope shaft 140.

The operator control module also includes a shaft collar 122, a shaft clamp trigger 124, a shaft anti-rotation pad 126, and a joystick portion 130. The shaft collar 122 is located on the opposite end of the operator control module 100 from the engaging mechanism 120, and the endoscope shaft 140 thus passes through the shaft collar 122 on one end of the operator control module and then through the engaging mechanism 120 on the other end of the operator control module. A handle extends outwardly from the engaging mechanism 120 and the shaft collar 122 such that the handle is spaced axially away from the axis of the endoscope shaft. As will be described in more detail below, the shaft clamp trigger 124 positioned between the U-shaped handle and the shaft anti-rotation pad 126 is utilized for engaging and disengaging the operator control module 100 from the endoscope shaft 140 and the shaft anti-rotation pad 126 is utilized to prevent the endoscope shaft 140 from rotating while the endoscope shaft 140 is fixedly engaged by the operator control module 100. The joystick portion 130 positioned on the U-shaped handle is utilized for the joystick for controlling the movement and operation of the distal end of the endoscope.

As will be described in more detail below, the operator control module 100 allows the endoscope shaft 140 to be rotated and the operator control module 100 to be decoupled from the endoscope shaft 140, such that the operator control module 100 can remain in the operator's preferred orientation, and then re-engaged to the endoscope shaft 140. The disengaging and the re-engagement capability is an improvement over other known endoscope systems in which the operator is required to twist the fixed operator control module as a way to apply torque to the shaft to rotate it axially to achieve the desired tip orientation in the patient. In accordance with the present invention, the endoscope is also provided with remotely powered tip articulation cables, which allows the operator control module 100 the freedom to not have to remain mechanically attached to the endoscope shaft 140 in a fixed position. It will be appreciated that the present invention allows the operator to have the ability to have the position of the operator control module 100 anywhere that is felt to be most comfortable or easiest to use. This degree of comfort and ease of use is an improvement over certain known endoscope designs, in which the orientation of the shaft determines where the operator has to try to manipulate the controls from (e.g., to rotate the shaft 180 degrees, in the prior art fixed systems, the operator control module would need to be rotated 180 degrees away from the user, which makes manipulating the controls difficult).

As illustrated in FIG. 1, the engaging mechanism 120 is shown to be a rotating locking collar which attaches to the proximal end of a break-out box on the endoscope shaft. Other similar mechanisms may be utilized to attach the operator control module to a rotary union on a fixed feature of the endoscope shaft. In another embodiment, the engaging mechanism 120 may instead be formed as a mechanism to clamp itself directly to the endoscope shaft 140. Whatever engagement mechanism is utilized, a key feature of the selectable orientation of the operator control module 100 is its ability to be disengaged and re-engaged from the endoscope shaft 140.

Another embodiment of the engaging mechanism 120 could be a caliper style set of pads that may be manually or remotely opened and closed for engaging the shaft. Another embodiment could be a "C" style clamping device that can be manually or remotely moved toward and away from contact with the endoscope shaft. Yet another embodiment could be a disengaging one-half of a clutch that is built into the operator control module with the other half of the clutch being built into a break-out box or other fixed feature on the shaft wherein one-half of the clutch in the operator control module may be manually or remotely moved to engage and disengage the other half of the clutch. Yet another embodiment could be a pressure pad that is mounted to a break-out box or other fixed feature on the shaft that can be manually or remotely moved to engage and disengage.

The selectable orientation of the operator control module 100 can either be wired back to the control box, or else can have a wireless method to communicate the commands of the operator back to the hardware in the control box. The control box contains pumps, a motor, valves, and other devices that are utilized to provide the desired features and operations of the endoscope.

Figure 2:
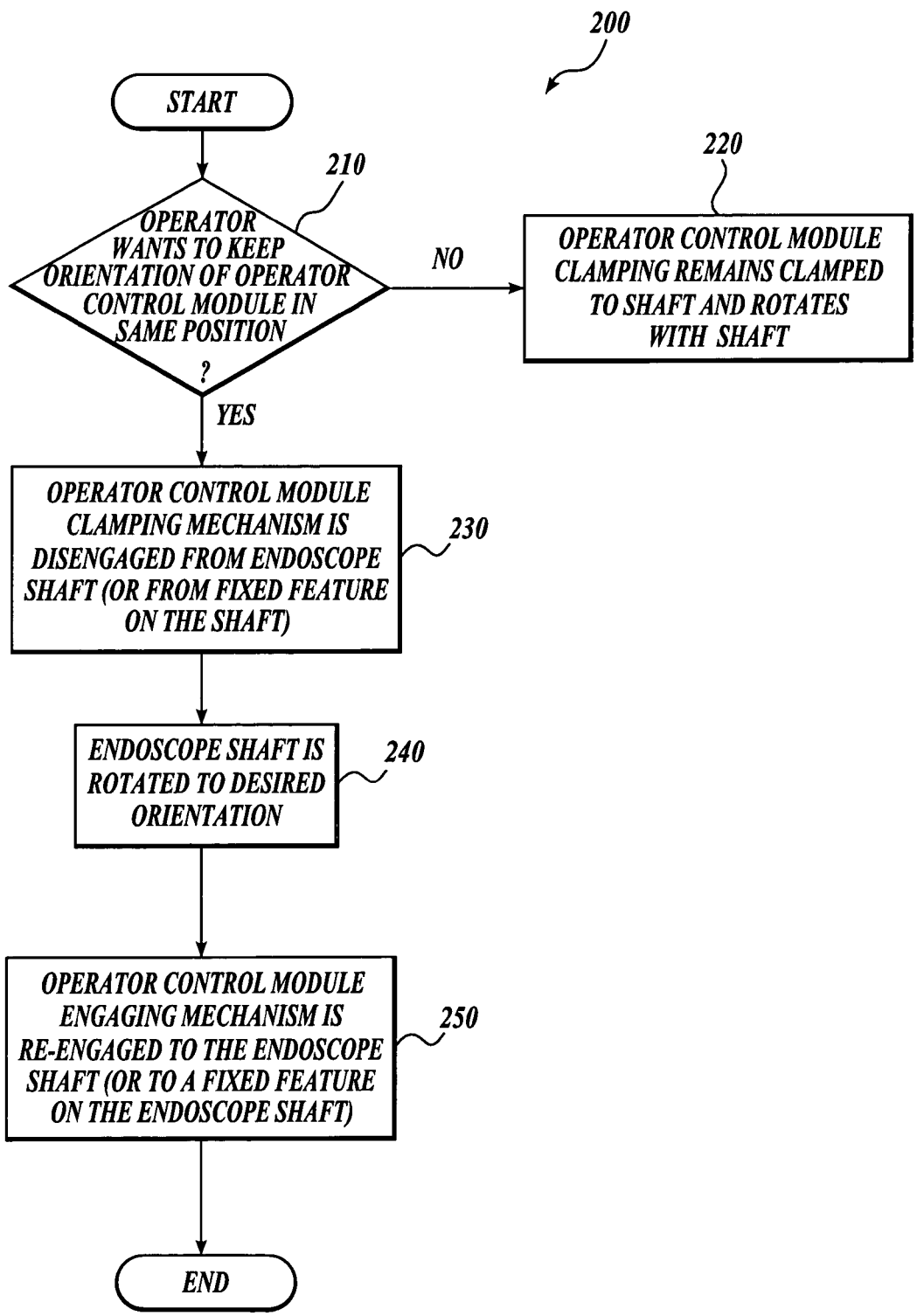
FIG. 2 is a flow diagram illustrative of a routine for disengaging and then re-engaging an operator control module from an endoscope shaft in order to keep the operator control module in a desired orientation once the endoscope shaft has been rotated.

FIG. 2 is a flow diagram illustrative of a routine 200 for engaging and disengaging the operator control module from the endoscope shaft. At a decision block 210, a determination is made as to whether the operator wants to keep the orientation of the operator control module in the same position. If the operator is not concerned about keeping the orientation the same, then the routine continues to a block 220, where the operator control module is not disengaged from the endoscope shaft, and thus remains clamped to the shaft and rotates with the shaft, thus changing orientation as the shaft rotates. If the operator does want to keep the orientation the same, then the routine continues to a block 230.

At block 230, the operator control module engaging mechanism is disengaged from the endoscope shaft (or from a fixed feature on the endoscope shaft). In other words, when the operator wants to rotate the endoscope shaft axially and does not want the position of the operator control module to be changed, the clamping mechanism is disengaged and the operator control module is thus allowed to rotate with respect to the shaft. At a block 240, the endoscope shaft is rotated to a desired orientation. At a block 250, the operator control module engaging mechanism is re-engaged to the endoscope shaft (or to a fixed feature on the shaft).

While the preferred embodiment of the invention has been illustrated and described, it will be appreciated that various changes can be made therein without departing from the spirit and scope of the invention.

The embodiments of the invention in which an exclusive property or privilege is claimed are defined as follow:

1. An operator control device for controlling an endoscope, comprising:
   a rotatable coupler that rotatably couples the operator control to a fixed feature on an endoscope shaft such that the operator control can be selectively rotated about the endoscope shaft but is prevented from moving along a length of the shaft;
   a shaft collar in line with the rotatable coupler such that an endoscope shaft can be releasably secured to the operator control device through the rotatable coupler and the shaft collar;

a U-shaped handle extending between the rotatable coupler and the shaft collar;

an endoscope control mounted on the U-shaped handle; and a trigger positioned between the U-shaped handle and the endoscope shaft for engaging and disengaging the operator control device from the endoscope shaft.

2. The operator control of claim 1, wherein the trigger operates an anti-rotation pad that prevents the endoscope shaft from rotating in the operator control device.

3. The operator control device of claim 1, wherein the U-shaped handle includes a joy stick for controlling the movement and operation of a distal end of the endoscope.

* * * * *